US006451609B1

United States Patent
Xu et al.

(10) Patent No.: US 6,451,609 B1
(45) Date of Patent: Sep. 17, 2002

(54) METHOD OF DETECTING GYNECOLOGICAL CARCINOMAS

(75) Inventors: Yan Xu, Pepper Pike; Yijin Xiao, Cleveland, both of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/448,800

(22) Filed: Nov. 24, 1999

Related U.S. Application Data (63) Continuation-in-part of application No. 09/139,841, filed on Aug. 25, 1998, now Pat. No. 5,994,141, which is a continuation of application No. 08/655,551, filed on May 30, 1996, now Pat. No. 5,824,555.

(51) Int. Cl.[7] ............................................... G01N 33/48
(52) U.S. Cl. ......................................... 436/64; 436/813
(58) Field of Search ................................... 436/64, 813

(56) References Cited

U.S. PATENT DOCUMENTS

| | | |
|---|---|---|
| 4,999,344 A | 3/1991 | Jett-Tilton et al. |
| 5,277,917 A | 1/1994 | Xu et al. |
| 5,326,690 A | 7/1994 | Xu et al. |
| 5,595,738 A | 1/1997 | Pomato et al. |
| 5,824,555 A | 10/1998 | Xu et al. |
| 5,994,141 A | 11/1999 | Xu et al. |

FOREIGN PATENT DOCUMENTS

| WO | WO 98/43093 | * 10/1998 |
|---|---|---|

OTHER PUBLICATIONS

Translation of abstract of article by Misako Okita, *Bulletin of the department of health and welfare*, Okayama Prefectural University, vol. 1–1, pp. 29–35, 1994.

"Effect of Lysophospholipids on Signaling in the Human Jurkat T Cell Line" by Xu, et al., *Journal of Cellula Physiology*, 163:441–450 (1995).

"Lysophospholipids activate ovarian and breast cancer cells" by Xu, et al., *Biochem. J.*, (1995) 309, 933–940.

"Characterization of an Ovarian Cancer Activating Factor in Ascites from Ovarian Cancer Patients" by Xu, et al. *Clinical Cancer Research*, vol. 1, pp. 1223–1232, Oct. 1995.

"Growth factor–like effects of lysophatidic acid, a novel lipid mediator" by Jalink, et al., *Biochemica et Biophysica Acta*, 1198 (1994) 185–196.

"Lysophatidic Acid, a Multifunctional Phospholipid Messenger" by Mooleanaar, *The Journal of Biological Chemistry*, vol. 270, No. 2, pp. 12949–12952, Jun. 2, 1995.

"Lysophosphatidic acid possesses dual action in cell proliferation" by Tigyi, et al., *Proc. Natl. Acad. Sci. USA*, vol. 91, pp. 1908–1912, Mar. 1994.

(List continued on next page.)

*Primary Examiner*—Jill Warden
*Assistant Examiner*—Monique T. Cole
(74) *Attorney, Agent, or Firm*—Calfee, Halter & Griswold LLP (57) ABSTRACT

Methods for detecting or diagnosing gynecological carcinomas in a patient are provided. One method The method, which involves assaying for the presence of lysophosphatidic acid in a plasma sample of the patient, is useful for detecting ovarian carcinoma, cervical carcinoma, endometrial carcinoma, and peritoneal carcinoma. In a preferred embodiment the method comprises: providing a blood specimen from the patient, obtaining a plasma sample for the blood specimen under conditions which minimize the release of lysophosphatidic acid from the platelets in the blood specimen into the plasma, extracting lipids from the plasma, and detecting the presence of lysophosphatidic acid in the lipid. Another method involves assaying for the presence of lysophosphatidyl inositol in a bodily fluid, preferably plasma, from the subject.

5 Claims, 2 Drawing Sheets

OTHER PUBLICATIONS

"Decanoyl lysophosphatidic acid induces platelet aggregation through an extracellular action" by Watson, et al., *Biochem. J.*, (1985) 232, pp. 61–66.

"LPA: a novel lipid mediator with diverse biological actions" by Moolenaar, *Trends in Cell Biology*, vol. 4, pp. 213–218, Jun. 1994.

"Increased phosphatidic acid and decreased lysophosphatidic acid in response to thrombin is associated with inhibition of platelet aggregation" by Gerrard, et al., *Biochem. Cell Biol.*, vol. 71, pp. 432–439, 1993.

"Lysophosphatidic Acid as a Potential Biomarker for Ovarian Cancer and Other Gynecological Cancers" by Xu, et al., *The Journal of the American Medical Association*, vol. 280, No. 8, pp. 719–723, Aug. 26, 1998.

"Peptide and Lipid Growth Factors Decrease cis–Diamminedichloroplatinum–induced Cell Death in Human Ovarian Cancer Cells" by Frankel, et al., *Clinical Cancer Research*, vol. 2, pp. 1307–1313, Aug. 1996.

"Role of Growth Factors: Their Receptors and Signalling Pathways in the Diagnosis, Prognosis, Follow–Up and Therapy of Ovarian Cancer" by Mills, et al., *Diagn Oncol*, 1992;2:39–54.

"Phorbol 12–Myristate 13–Acetate Simulates Lysophosphatidic Acid Secretion from Ovarian and Cervical Cance Cells but Not from Breast or Leukemia Cells" by Shen, et al., *Gynecologic Oncology*, 71, 364–368 (1998).

"Elevated Levels and Altered Fatty Acid Composition of Plasma Lysophosphatidylcholine(LYSOPC) in Ovarian Cancer Patients" by Okita, et al., *Int. J. Cancer*, 71, 31–34 (1997).

"Activation of human ovarian cancer cells: role of lipid factors in ascitic fluid" by Xu, et al, Chapman & Hall Medical, London, Glasgow, Weinheim, New York, Tokyo, Melbourne, Madras, pp. 121–135 (1994).

"Malignant effusions contain lysophosphatidic acid (LPA-)–like activity" by Westermann, et al., *Annals of Oncology*, 9, pp. 437–442 (1998).

"Soluble Interleukin–2 Receptor Alpha is Elevated in Sera of Patients with Benign Ovarian Neoplasms and Epithelial Ovarian Cancer" by Hurteau, et al, *Cancer*, vol. 76, No. 9, pp. 1615–1620, Nov. 1, 1995.

"A Putative New Growth Factor in Ascitic Fluid from Ovarian Cancer Patients: Identification, Characterization, and Mechanisms of Action" by Mills, et al., *Cancer Research*, 48, 1066–1071, Mar. 1, 1988.

"Ascitic Fluid from Human Ovarian Cancer Patients Contains Growth Factors Necessary for Intraperitoneal Growth of Human Ovarian Adenocarcinoma Cells" by Mills, et al., *J. Clin. Invest.*, vol. 86, pp. 851–855, Sep., 1990.

"Levels of soluble interleukin–2 receptor–$\alpha$ are elevated in serum and ascitic fluid from epithelial ovarian cancer patient" by Hurteau, et al., *Am J Osbstet Gynecol*, vol. 170, No. 3, pp. 918–928, Mar. 1994.

"Lysophosphatidylcholine Stimulates Activator Protein 1 and the c–Jun N–terminal Kinase Activity" by Fang, et al., *The Journal of Biological Chemistry*, vol. 272, No. 21, pp. 13683–13689, May 23, 1997.

"Induction of In Vitro Tumor Cell Invasion of Cellular Monoplayers by Lysophosphatidic Acid or Phospholipase D" by Imamura, *Biochemical and Biophysical Research-Communications*, vol. 193, No. 2, pp. 497–503, Jun. 15, 1993.

"Analysis of the Proliferative Response to Lysophosphatidic Acid in Primary Cultures of mammary Epithelium: Differences between Normal and Tumor Cells" by Imagawa, et al., *Experimental Cell Research*, 216, 178–186 (1995).

"The bioactive phospholipid acid is released from activated platelets" by Eichholtz, et al., *Biochem J.*, 291, (1993), pp. 677–680.

"Lysophosphatidic acid: G–protein signalling and cellular responses" by Moolenaar, et al., *Cell Regulation*, pp. 168–173.

Abstract #710, "Lysophosphatidic acd, a diagnostic biomarker for ovarian and other gynecological cancers" by Xu, et al., *Proceedings of the American Association for Cancer Research*, vol. 38, Mar. 1997, p. 106.

"Abnormality in plasma lysophosphatidic acid of ovarian cancer patients" by Okita, et al., *Bulletin of the department of health and welfare*, Okayama Prefectural University, vol. 1–1, 1994, pp. 29–35.

* cited by examiner

METHOD OF DETECTING GYNECOLOGICAL CARCINOMAS

CROSS REFERENCE TO RELATED APPLICATIONS

This application is a continuation-in-part of U.S. application Ser. No. 09/139,841 filed on Aug. 25, 1998, now U.S. Pat. No. 5,994,141, which is a continuation of the U.S. application Ser. No. 08/655,551, filed on May 30, 1996, now U.S. Pat. No. 5,824,555.

BACKGROUND OF THE INVENTION

Gynecological carcinomas such as ovarian carcinoma, cervical carcinoma, endometrial carcinoma and peritoneal carcinoma are among the most frequent causes of cancer death among women in the United States and Europe. It is estimated that ovarian carcinoma alone will be responsible for 14,800 deaths in 1996 in the United States. This dismal outcome is due, at least in part, to an inability to detect the ovarian carcinoma at an early stage of tumor development. When ovarian carcinoma is diagnosed at an early stage, the cure rate approaches 90%. In contrast, the 5 year outlook for women with advanced disease remains poor with no more than a 15% survival rate. Thus, early diagnosis is one of the most effective means of improving the prognosis for ovarian carcinoma.

Transvaginal sonography is the most sensitive of the currently available techniques used for detecting ovarian tumors. However, transvaginal sonography is non-specific, i.e. it will detect benign as well as malignant tumors. Accordingly, detection of an ovarian tumor by transvaginal sonography must be followed by a second diagnostic procedure which is able to distinguish benign tumors from malignant tumors. Moreover, transvaginal sonography is very expensive and, therefore, not useful as a screening procedure for large numbers of patients.

Typically, benign ovarian tumors are distinguished from malignant ovarian tumors by surgical procedures such as biopsy of the mass or aspiration of the mass and cytological examination of the cells that are surgically removed from the patient. However, these techniques are highly invasive, expensive, and in the case of aspiration can lead to release of cancerous cells into the peritoneum.

The antigenic determinant CA 125, which is a high molecular weight mucin-like glycoprotein, is the current serum biomarker of choice for screening for ovarian carcinomas. However, CA 125 testing suffers from two main limitations. First of all, it is not very sensitive. For example, elevated serum CA 125 levels, i.e. levels above the cut-off point of 35 U/ml, are present in fewer than 50% of the patients with Stage I ovarian carcinoma. Taylor, K. J. W. and Schwartz, P. E., "Screening for Early Ovarian Cancer," Radiology, 192:1–10, 1994. In addition, CA 125 testing is not very specific. For example, approximately 25% of patients. with benign gynecological diseases also have elevated serum levels of CA 125. Moreover, liver disease such as cirrhosis, even without ascites, elevates serum CA 125 levels above 35 U/ml. Taylor, K. J. W. and Schwartz, P. E., "Screening for Early Ovarian Cancer," Radiology, 192:1–10, 1994.

Accordingly, it would be desirable to have a new, simple, noninvasive or marginally invasive methods for detecting gynecological carcinomas, particularly ovarian carcinomas. Methods which are sufficiently sensitive to identify those subjects with early stage ovarian carcinoma, and sufficiently specific to distinguish between benign and malignant gynecological carcinomas are especially desirable.

SUMMARY OF THE INVENTION

The present invention provides new, simple, marginally-invasive methods for detecting the presence of gynecological carcinomas, particularly ovarian carcinomas, in a subject.

One method comprises assaying for the presence of lysophosphatidic acid in a plasma sample. The presence of lysophosphatidic acid in the plasma sample indicates that a gynecological carcinoma is present in the subject. In a preferred embodiment, the method comprises preparing a plasma sample which is substantially free of platelets from a blood specimen from the subject, preparing a lipid extract from said plasma sample, and assaying for the presence of lysophosphatidic acid in said lipid extract. Because the method is sufficiently sensitive to detect ovarian carcinoma in subjects with early stage ovarian carcinoma, sufficiently specific to distinguish benign gynecological carcinomas from malignant gynecological carcinomas, and marginally invasive, the method is especially useful for screening patients for ovarian carcinomas. The method also detects the presence of endometrial carcinoma, peritoneal carcinoma, and cervical carcinoma in a subject. Accordingly, the method is useful for screening for more than one gynecological carcinoma.

Another method comprises assaying for the presence of lysophophatidyl inositol in a bodily fluid, preferably a blood sample from the subject. Preferably, the concentration of the lysophosphatidyl inositol in the bodily fluid is determined.

BRIEF DESCRIPTION OF THE FIGURES

FIG. 1A show the representative mass spectra of lysophospholipids from patients with ovarian cancer (FIG. 1A) and from healthy control subjects (FIG. 1B).

DETAILED DESCRIPTION OF THE INVENTION

The present invention provides new, simple methods for detecting or diagnosing gynecological carcinomas, particularly ovarian carcinomas, in a subject or patient. One method comprises assaying for the presence of lysophosphatidic acid in a blood plasma sample from the patient. Preferably, the blood plasma sample is substantially free of platelets. As described herein, a plasma sample is substantially free of platelets when it contains less than 95% of the platelets present in the original blood specimen obtained from the patient. In a preferred embodiment, the method comprises providing a whole blood specimen from the patient, obtaining a plasma sample which is substantially free of platelets from the whole blood specimen, extracting lipids from the blood plasma sample, and assaying for the presence of lysophosphatidic acid in the lipid extract.

Preferably, the blood plasma sample is obtained under conditions which minimize the release of lysophosphatidic acid from platelets which are present in the whole blood specimen. Such conditions include, for example, collecting the whole blood specimen from the subject in tubes that contain an anti-coagulant. Suitable anti-coagulants include, for example, heparin and chelating agents. It is preferred that the whole blood specimen be collected in the presence of a chelating agent, such as for example ethylenediaminetetraacetic acid (EDTA) or sodium citrate, more preferably EDTA, since chelating agents both reduce phospholipase activity in the sample and prevent clotting of the whole blood specimen.

The blood plasma typically is obtained by centrifuging the whole blood specimen to pellet the blood cells in the whole blood specimen and collecting the supernatant, which represents the major portion of the blood plasma in the whole blood specimen.

Substantially all of the lipids, particularly the phospholipids, in the plasma sample are then extracted, preferably by a lipid extraction procedure which recovers at least 80% of the lysophosphatidic acid from the plasma sample. More preferably, the lipid extraction procedure recovers at least 85% of the LPA in the plasma sample. An example of a preferred lipid extraction procedure comprises the steps of: acidifying the blood plasma sample; mixing the acidified blood plasma sample with an organic solvent to provide an aqueous phase and an organic phase, wherein the phospholipids preferentially distribute to the organic phase; and recovering the organic phase to provide a lipid extract which contains greater than 80% of the lysophosphatidic acid in the plasma sample. Preferably, hydrochloric acid is used to acidify the blood plasma sample. Preferably the final concentration of acid in the acidified plasma sample is from about 0.2 N to about 2.0 N.

Suitable organic solvents for extracting lysophosphatidic acid from the acidified plasma sample include for example butanol, isopropanol, and mixed organic solvents which comprise a polar organic solvent, such as for example methanol, and a non-polar organic solvent, such as for example chloroform. Preferably the organic solvent is a mixture of methanol and chloroform at a 2:1 ratio.

The lysophosphatidic acid, also referred to herein as "LPA," is then separated from the other phospholipids in the organic phase using conventional techniques. One such technique involves separation by thin-layer chromatography to provide an LPA band.

The amount of lysophosphatidic acid in the LPA band is then quantified using conventional techniques. The quantification technique used depends upon the amount of blood specimen provided by the subject. For example, if the size of the blood specimen is 2 ml or less, it is preferred that a quantification technique which is capable of detecting picomole amounts of LPA be used. Suitable techniques for detecting picomole amounts of LPA include, for example, hydrolyzing the isolated LPA fraction and then quantifying the amount of each fatty acid in the hydrolysate by gas chromatography. If the size of the blood specimen is 20 ml or greater, a technique which is capable of detecting nanomole amounts of LPA, such as for example total phosphorous determination in the LPA fraction, is suitable.

Another method comprises assaying for the presence of lysophosphatidyl inositol (LPI) in a bodily fluid from the subject. Preferably, the bodily fluid is blood, more preferably plasma. One method of assaying for the presence of LPI in the bodily fluid involves extraction of lipids from the sample, separation of the lipids by thin-layer chromatography and direct analysis with electrospray ionization mass spectrometry (ESI-MS). This method has the following advantages: i) soft ionization detects intact molecular species and therefore the true identities of lipid molecules; ii) structures of interesting ion peaks can be determined through tandem,-MS (MS/MS) or liquid chromatography/tandem mass spectrometry (LC/MS/MS) analysis; iii) it simultaneously detects many molecular species, including lipids with different fatty acid chains; iv) it is highly sensitive (typically in the femtomole to low picomole range) and v) the assay can be easily adapted to an autosampler.

Preferably, the method further comprises determining the levels or concentration of LPI in said bodily fluid. In accordance with the present invention, it has been determined that females with ovarian carcinoma have higher levels or concentrations of LPI in their plasma than healthy subjects. Preferably, the level or concentration of LPI in the bodily fluid is then compared to a standard value. The standard value is based upon the levels of LPI found in comparable samples obtained from a population of healthy subjects.

Standard values of LPI in a bodily fluid are for example, mean levels, median levels, or preferably "cut-off" levels. Cut-off values are established by assaying a large sample of healthy individuals and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. Preferably, the levels of both LPA and LPI in the bodily fluid are determined. In accordance with the present invention, it has been determined that a combined test value which is based on the concentration of both LPA and LPI in plasma from the subject is a better indicator of ovarian carcinoma than a test value which is based on the concentration of LPA or LPI alone. The combined test value is compared to a combined standard value which is based on the concentrations of LPA and LPI found in plasma from healthy subjects.

The methods disclosed herein are useful for detecting gynecological carcinomas such as cervical carcinoma, endometrial carcinoma, peritoneal carcinoma, and ovarian carcinoma, that is, epithelial ovarian cancer. Epithelial ovarian cancer includes serous tumors, mucinous tumors, endometroid tumors, clear cell tumors, undifferentiated carcinoma, mixed epithelial tumors, and unclassified epithelial tumors.

The methods disclosed herein are especially useful for assessing the malignancy of an ovarian mass in a patient and for detecting ovarian carcinomas at the early surgical stage of development in a patient, that is Surgical Stage I and Surgical Stage II, as well as at the later stages of development, that is Surgical Stage III and Surgical Stage IV. Surgical stage represents the severity of disease with Stage I being least severe and Stage IV being the most severe. According to criteria established by the International Federation of Gynecology and Obstetrics, the ovarian carcinoma is limited to the ovaries and may or may not include ascites in Stage I ovarian carcinoma. In Stage II, there is pelvic extension of the carcinoma and possibly extension to the uterus or fallopian tubes. Stage III ovarian carcinoma is characterized by abdominal metastases. In Stage IV, there is distant metastases of the carcinoma outside of the peritoneal cavity.

The methods disclosed herein are simple, marginally invasive, and require only a blood specimen from the subject. Thus, such methods are also useful for screening patients who have not been previously diagnosed as carrying carcinoma, particularly patients who are at risk for gynecological carcinomas, especially ovarian carcinoma. Such patients include women at elevated risk by virtue of a family history of the disease, premenopausal women with anovulatory cycles, and postmenopausal women.

The present invention is further described by the examples which follow. Such examples, however, are not to be construed as limiting in any way either the spirit or the scope of the present invention.

EXAMPLE 1

Plasma samples were obtained from blood specimens provided by eighty-four female subjects. A whole blood specimen of approximately 2 ml was collected from each of the subjects in a 5 ml vacutainer tube containing 7.2 mg of EDTA.

Obtaining a Plasma Sample from the Whole Blood Specimen

The whole blood specimen was centrifuged at 580×g for 5 minutes to provide a pellet of the blood cells and platelets and a supernatant. The supernatant was transferred to a siliconized microcentrifuge tube and centrifuged for 5 minutes at 8000×g to provide a second pellet and a plasma supernatant. The plasma supernatant was either processed immediately or stored at −70° C.

Extracting LPA from a Plasma Sample

Extraction of lipids, particularly LPA from the plasma sample was performed at 0–4° C. Each 1 mL sample of plasma was acidified by adding 0.2 mL of 12 N HCl to provide a plasma sample with a final concentration of HCl of approximately 2.0 N. After mixing, 4 ML of mixed organic solvent comprising a 2:1 ratio of methanol/chloroform was added to the acidified plasma and the mixture was vortexed for 1 minute and incubated on ice for 10 minutes. 1 mL of chloroform and 1.25 mL of $H_2O$ were added to the mixture. After mixing thoroughly, the mixture was centrifuged at 1000×g for 10 minutes at 4° C. The lower organic layer was transferred to a new glass tube and dried at 40° C. under nitrogen to provide a phospholipid extract.

The total recovery rate and reproducibility of this extraction procedure was examined by adding 10 nmol of synthetic oleoyl-LPA to three parallel plasma samples lacking endogenous oleoyl-LPA. The samples were extracted by the present procedure and the amount of oleoyl-LPA in each sample quantified. This analysis indicated that the average recovery of LPA by the present extraction procedure was 92.7% with a standard error of ±5.6%.

Isolating the LPA in the Lipid Extract

Each lipid extract was dissolved in 50 µl of a 2:1 methanol/chloroform mixture and loaded onto a single lane of a precoated silica-gel 60 TLC plate (20×20 cm, layer thickness 250 mm) obtained from EM Science, Darmstadt, Germany. A 50 µl aliquot of a 2:1 methanol/chloroform mixture containing 10 to 50 µg of oleoyl-LPA obtained from Avanti Polar-Lipids, Inc. was loaded onto one outside lane of the plate and a 50 µl aliquot of chloroform containing 10 to 50 µg of lysophosphatidylcholine obtained from Sigma Chemical Company was loaded onto the opposite outside lane of the plate. The oleoyl-LPA and lysophosphatidylcholine were used as migration references for locating the LPA fractions on the plate. The lipids were developed at room temperature for approximately 3 hours with a mixture of chloroform-methanol-ammonium hydroxide (65:35:5.5). Then the outside lanes containing the oleoyl LPA and lysophosphatidylcholine standards were sprayed with 0.1% 8-anilino-1-naphthalene-sulfonic acid and visualized under ultraviolet light.

Each of the isolated LPA fractions in the lanes loaded with lipid extracts from the plasma samples were scraped from the plates into separate 15 mL disposable glass centrifuge tubes from Kimble, Vineland, N.J. The LPA fractions included all of the lipids that migrated to a distance on the plate which corresponded to the Rf of the oleolyl-LPA standard and extended to but was less than the Rf of the lysophosphatidylcholine standard.

Measuring the Amount of LPA Isolated from Each Sample 2 mL of 1M ethanolic KOH were added to each tube containing the isolated LPA fractions. The tubes were then incubated at 60° C. for 1 hour to hydrolyze the LPA present in the tube. After cooling, 5 µl of internal standard solution contains methyl behenate, 1.5 mg/mL in chloroform, 1 mL of 6N HCl. 5 mL of $H_2O$ and 5 mL of ethyl ether were added to the hydrolysate. The mixture was vortexed for 30 seconds and centrifuged at 1000×g for 10 minutes. Then, the upper layer was transferred into a new glass tube and dried at 40° C. under nitrogen. The residue, which contained fatty acids released from the LPA, was dissolved in 0.6 mL of petroleum ether and the dissolved, fatty acids were transmethylated by adding 1 mL of $BCl_3$-methanol reagent to each tube and incubating at 100° C. for 10 minutes. $BCl_3$ methanol was obtained from Supelco Inc., Bellefonte, Pa. The fatty acid methyl esters were extracted with 1 ml of petroleum ether. The mixture was vortexed for 10 seconds and centrifuged at 1000×g for 5 minutes. The top layer was transferred to a 3.7 mL screw-topped Supelco sample vial and dried at 40° C. under nitrogen. The residue was then dissolved in 25 µl of chloroform and 5–15 µl of the chloroform solution was used for analysis by gas chromatography.

GC Analysis of the Fatty Acids Released from LPA by Hydrolysis

A Hewlett-Packard Model 5710A gas chromatograph, equipped with a fused silica column (25 m×0.2 mm) coated with 3% SP-2310, 2% SP-2300 on 100/120 Chromosorb WAW from Supelco Inc., was used to measure the amount of each fatty acid in each of the samples. The gas chromatograph conditions were as follows: the oven starting temperature was 185° C.; after 2 minutes, the temperature was increased at 2° C./minutes to 230° C., and held for 4 minutes; the injector temperature was 200° C.; the detector temperature was 300° C.; nitrogen was the carrier gas at a flow rate of 30 ml/minutes at 50 PSI; airflow rate was 240 mu/minutes at 24 PSI; hydrogen flow was 30 ml/min at 15 Psi. A flame ionization detector was used to detect the fatty acid methyl esters. Two standard curves were obtained using two fatty acid methyl esters standard mixtures obtained from Nu Check Prep. Inc., Elysian, Minn. The two standard mixtures included different combinations of the esters of methyl palmitate, methyl stearate, methyl oleate, methyl linoleate, methyl arachidonate and methyl behanate. The retention times were 3.8 min for methyl palmitate, 6.7 min for methyl stearate, 7.3 min for methyl oleate, 8.3 min for methyl linoleate, 14.0 min for methyl arachidonate and 15.3 min for methyl behenate (internal standard).

The concentrations of each fatty acid in each sample were calculated and added together to obtain the concentration of total LPA in each plasma sample. The concentrations in µM of each LPA species and of total LPA in each of the samples are presented in Table I.

Each of the female subjects also underwent one or more routine diagnostic procedures to determine whether she was healthy or had an active disease. The diagnostic procedures included, where appropriate, clinical examination, clinical chemistries, and surgical evaluation of any masses detected. On the basis of these routine diagnostic procedures, the patients were diagnosed as being healthy or as having an active form of one of the diseases listed in Table I.

TABLE I

LPA Levels (μM) in Plasma of Subjects of the Example

| Diagnosis | LPA(P) | LPA(S) | LPA(O) | LPA(L) | LPA(A) | LPA(D) | TOTAL LPA |
|---|---|---|---|---|---|---|---|
| 1. Ovarian Carcinoma Stage I | | | | | | | |
| #1 | 9.97 | 12.84 | 4.39 | 2.83 | 2.29 | B.D. | 32.32 |
| #2 | 10.78 | 10.28 | 1.84 | B.D. | B.D. | B.D. | 22.9 |
| #3 | 1.39 | 0.40 | 0.87 | 2.01 | B.D. | B.D. | 4.67 |
| 2. Ovarian Carcinoma Stage II | | | | | | | |
| #1 | 0.78 | 2.17 | 0.68 | 0.98 | 0.41 | B.D. | 5.02 |
| 3. Ovarian Carcinoma Stage III | | | | | | | |
| #1 | 8.87 | 9.15 | 3.98 | 4.17 | 3.32 | B.D. | 29.49 |
| #2 | 7.90 | 6.97 | 3.46 | 8.97 | 6.45 | B.D. | 33.75 |
| #3 | 9.59 | 6.96 | 1.59 | 1.64 | 2.56 | B.D. | 22.34 |
| #4 | 11.09 | 7.62 | 5.72 | 11.78 | 6.85 | B.D. | 43.06 |
| #5 | 5.64 | 4.14 | B.D. | B.D. | B.D. | B.D. | 9.78 |
| #6 | 3.10 | 4.62 | 1.58 | 3.18 | 1.59 | B.D. | 14.07 |
| #7 | 2.13 | 1.80 | 0.39 | 0.91 | B.D. | B.D. | 5.23 |
| #8 | 0.81 | 1.56 | 0.77 | B.D. | B.D. | B.D. | 3.14 |
| #9 | 3.30 | 6.22 | 2.28 | 5.40 | 5.17 | B.D. | 22.37 |
| #10 | 2.37 | 4.33 | 1.56 | 0.77 | 0.92 | B.D. | 9.95 |
| #11 | 5.34 | 8.32 | 2.68 | 1.85 | 2.39 | B.D. | 20.58 |
| #12 | 8.97 | 10.23 | 11.39 | 13.50 | 8.96 | 3.12 | 56.17 |
| #13 | 1.08 | 0.89 | 0.31 | 0.25 | B.D. | B.D. | 2.53 |
| #14 | B.D. | 1.82 | 0.43 | 2.42 | 2.42 | B.D. | 5.84 |
| 4. Ovarian Carcinoma Stage IV | | | | | | | |
| #1 | 3.61 | 4.91 | 2.09 | 1.16 | B.D. | B.D. | 11.77 |
| 5. Peritoneal Carcinoma | | | | | | | |
| #1 | 14.22 | 9.93 | 3.08 | 3.79 | 1.94 | B.D. | 32.96 |
| #2 | 3.19 | 6.29 | 0.68 | 6.25 | B.D. | B.D. | 16.41 |
| #3 | 2.65 | 2.29 | 0.13 | B.D. | B.D. | B.D. | 5.07 |
| #4 | 12.81 | 11.45 | 12.50 | 14.92 | 9.19 | 2.34 | 63.21 |
| #5 | 0.70 | 1.17 | B.D. | B.D. | B.D. | B.D. | 1.87 |
| #6 | B.D. | B.D. | B.D. | B.D. | B.D. | B.D. | B.D. |
| #7 | 3.89 | 4.01 | 3.94 | 4.51 | 2.84 | B.D. | 19.19 |
| #8 | 3.11 | 3.15 | 1.72 | 2.40 | 1.70 | B.D. | 12.08 |
| #9 | 1.16 | B.D. | B.D. | B.D. | 0.28 | B.D. | 1.44 |
| 6. Endometrial Carcinoma | | | | | | | |
| #1 | 8.46 | 9.45 | 3.85 | 4.83 | 2.23 | B.D. | 28.82 |
| #2 | 11.01 | 11.31 | 2.33 | 1.03 | B.D. | B.D. | 25.68 |
| #3 | 6.84 | 15.84 | 12.62 | 18.88 | 9.05 | B.D. | 63.23 |
| #4 | 7.68 | 7.27 | 3.53 | 5.67 | 7.24 | B.D. | 31.39 |
| #5 | 1.71 | 1.65 | 0.59 | B.D. | B.D. | B.D. | 3.95 |
| #6 | 6.19 | 7.65 | 2.59 | 5.27 | 2.89 | B.D. | 24.59 |
| #7 | 21.15 | 5.16 | 16.41 | 20.98 | B.D. | B.D. | 54.56 |
| 7. Cervical Carcinoma | | | | | | | |
| #1 | 5.94 | 5.60 | 2.99 | 1.19 | 2.10 | B.D. | 17.82 |
| #2 | 12.45 | 11.18 | 6.72 | 10.44 | 6.53 | B.D. | 47.32 |
| #3 | 0.86 | 1.14 | B.D. | B.D. | B.D. | B.D. | 2.00 |
| #4 | 15.29 | 12.98 | 8.27 | 5.68 | 8.97 | B.D. | B.D. |
| 8. Healthy | | | | | | | |
| #1 | B.D. | B.D. | B.D. | B.D. | B.D. | B.D. | B.D. |
| #2 | B.D. | B.D. | 0.42 | B.D. | B.D. | B.D. | 0.42 |
| #3 | B.D. | B.D. | B.D. | B.D. | B.D. | B.D. | B.D. |
| #4 | B.D. | B.D. | B.D. | B.D. | B.D. | B.D. | B.D. |
| #5 | B.D. | B.D. | B.D. | B.D. | B.D. | B.D. | B.D. |
| #6 | B.D. | 1.94 | 0.21 | B.D. | B.D. | B.D. | 2.15 |
| #7 | B.D. | B.D. | B.D. | B.D. | B.D. | B.D. | B.D. |
| #8 | B.D. | B.D. | B.D. | B.D. | B.D. | B.D. | B.D. |
| #9 | B.D. | B.D. | B.D. | B.D. | B.D. | B.D. | B.D. |
| #10 | B.D. | B.D. | B.D. | B.D. | B.D. | B.D. | B.D. |
| #11 | B.D. | B.D. | B.D. | B.D. | B.D. | B.D. | B.D. |
| #12 | B.D. | B.D. | B.D. | B.D. | B.D. | B.D. | B.D. |
| #13 | B.D. | B.D. | 0.42 | B.D. | B.D. | B.D. | 0.42 |
| #14 | B.D. | B.D. | B.D. | B.D. | B.D. | B.D. | B.D. |
| #15 | B.D. | B.D. | B.D. | B.D. | B.D. | B.D. | B.D. |
| #16 | B.D. | B.D. | B.D. | B.D. | B.D. | B.D. | B.D. |
| #17 | 0.48 | 0.69 | B.D. | B.D. | B.D. | B.D. | 1.17 |
| #18 | B.D. | B.D. | B.D. | B.D. | B.D. | B.D. | B.D. |
| #19 | B.D. | B.D. | B.D. | B.D. | B.D. | B.D. | B.D. |
| #20 | B.D. | B.D. | B.D. | B.D. | B.D. | B.D. | B.D. |

TABLE I-continued

LPA Levels (μM) in Plasma of Subjects of the Example

| Diagnosis | LPA(P) | LPA(S) | LPA(O) | LPA(L) | LPA(A) | LPA(D) | TOTAL LPA |
|---|---|---|---|---|---|---|---|
| #21 | B.D. | B.D. | B.D. | B.D. | B.D. | B.D. | B.D. |
| #22 | 4.93 | B.D. | B.D. | B.D. | B.D. | B.D. | 4.93 |
| #23 | B.D. | B.D. | B.D. | B.D. | B.D. | B.D. | B.D. |
| 9. Benign GYN Diseases | | | | | | | |
| #1 | B.D. | B.D. | B.D. | B.D. | B.D. | B.D. | B.D. |
| #2 | B.D. | B.D. | B.D. | B.D. | B.D. | B.D. | B.D. |
| #3 | B.D. | B.D. | B.D. | B.D. | B.D. | B.D. | B.D. |
| 10. Sarcoma | | | | | | | |
| #1 | B.D. | B.D. | B.D. | B.D. | B.D. | B.D. | B.D. |
| #2 | B.D. | B.D. | B.D. | B.D. | B.D. | B.D. | B.D. |
| #3 | B.D. | B.D. | B.D. | B.D. | B.D. | B.D. | B.D. |
| #4 | B.D. | 2.08 | 0.99 | 1.43 | 3.48 | B.D. | 7.97 |
| 11. Breast Cancer | | | | | | | |
| #1 | B.D. | B.D. | B.D. | B.D. | B.D. | B.D. | B.D. |
| #2 | B.D. | B.D. | 0.42 | B.D. | B.D. | B.D. | 0.42 |
| #3 | B.D. | B.D. | B.D. | B.D. | B.D. | B.D. | B.D. |
| #4 | B.D. | B.D. | B.D. | B.D. | B.D. | B.D. | B.D. |
| #5 | B.D. | B.D. | B.D. | B.D. | B.D. | B.D. | B.D. |
| #6 | B.D. | B.D. | B.D. | B.D. | B.D. | B.D. | B.D. |
| #7 | B.D. | B.D. | B.D. | B.D. | B.D. | B.D. | B.D. |
| #8 | B.D. | B.D. | B.D. | B.D. | B.D. | B.D. | B.D. |
| #9 | B.D. | B.D. | B.D. | B.D. | B.D. | B.D. | B.D. |
| #10 | B.D. | B.D. | B.D. | B.D. | B.D. | B.D. | B.D. |
| #11 | B.D. | B.D. | B.D. | B.D. | B.D. | B.D. | B.D. |
| 12. Leukemia | | | | | | | |
| #1 | B.D. | B.D. | B.D. | B.D. | B.D. | B.D. | B.D. |
| #2 | B.D. | B.D. | B.D. | B.D. | B.D. | B.D. | B.D. |
| #3 | B.D. | B.D. | B.D. | B.D. | B.D. | B.D. | B.D. |
| #4 | B.D. | B.D. | B.D. | B.D. | B.D. | B.D. | B.D. |

LPA(P): palmitoyl - LPA
LPA(S): stearoyl - LPA
LPA(O): oleoyl - LPA
LPA(L): linolenyl - LPA
LPA(A): arachidyl - LPA
LPA(D): docosahexanyl - LPA
B.D.: below detection
N.A.: Not available The average concentrations±SE of each LPA species in the plasma of patients diagnosed as having a gynecological carcinoma and the average concentration±SE of each LPA species in the plasma of patients diagnosed as not having a gynecological carcinoma are presented in Table II. The average concentrations±SE of total LPA in the plasma of patients with the gynecological carcinomas and the average concentrations±SE of total LPA in the plasma of patients without gynecological carcinomas are presented in Table III. The statistical power calculations were performed using the Wilcoxon Rank Sum statistical test as described by W. J. Conover in Practical Nonparametric. 0.1 μM was used in calculations where LPA levels were below detection.

TABLE II

Average Concentration of Individual LPA Species in the Plasma of Subjects from the Example

| Diagnosis | N | LPA | Mean | SE | SD | Median | Min | Max |
|---|---|---|---|---|---|---|---|---|
| Healthy | 23 | LPA(P) | 0.33 | 0.21 | 1.01 | 0.10 | 0.10 | 4.93 |
| | | LPA(S) | 0.21 | 0.08 | 0.40 | 0.10 | 0.10 | 1.94 |
| | | LPA(O) | 0.10 | 0.00 | 0.02 | 0.10 | 0.10 | 0.21 |
| | | LPA(L) | 0.10 | 0.00 | 0.00 | 0.10 | 0.10 | 0.10 |
| | | LPA(A) | 0.10 | 0.00 | 0.00 | 0.10 | 0.10 | 0.10 |
| | | LPA(D) | 0.10 | 0.00 | 0.00 | 0.10 | 0.10 | 0.10 |
| Ovarian Carcinoma | 19 | LPA(P) | 5.10 | 0.88 | 3.85 | 3.61 | 0.10 | 11.09 |
| | | LPA(S) | 5.54 | 0.83 | 3.61 | 4.91 | 0.40 | 12.84 |
| | | LPA(O) | 2.43 | 0.61 | 2.66 | 1.59 | 0.10 | 11.39 |
| | | LPA(L) | 3.27 | 0.91 | 3.96 | 1.85 | 0.10 | 13.50 |
| | | LPA(A) | 2.32 | 0.62 | 2.70 | 1.59 | 0.10 | 8.96 |
| | | LPA(D) | 0.26 | 0.16 | 0.69 | 0.10 | 0.10 | 3.12 |

TABLE II-continued

Average Concentration of Individual LPA Species in the Plasma of Subjects from the Example

| Diagnosis | N | LPA | Mean | SE | SD | Median | Min | Max |
|---|---|---|---|---|---|---|---|---|
| Peritoneal Carinoma | 9 | LPA(P) | 4.65 | 1.73 | 5.19 | 3.11 | 0.10 | 14.22 |
|  |  | LPA(S) | 4.28 | 1.38 | 4.14 | 3.15 | 0.10 | 11.45 |
|  |  | LPA(O) | 2.48 | 1.34 | 4.02 | 0.68 | 0.10 | 12.50 |
|  |  | LPA(L) | 3.59 | 1.61 | 4.83 | 2.40 | 0.10 | 14.92 |
|  |  | LPA(A) | 1.82 | 0.98 | 2.95 | 0.28 | 0.10 | 9.19 |
|  |  | LPA(D) | 0.35 | 0.25 | 0.75 | 0.10 | 0.10 | 2.34 |
| Endometrial Carcinoma | 7 | LPA(P) | 9.01 | 2.29 | 6.05 | 7.68 | 1.71 | 21.15 |
|  |  | LPA(S) | 8.33 | 1.71 | 4.52 | 7.65 | 1.65 | 15.84 |
|  |  | LPA(O) | 5.99 | 2.27 | 6.02 | 3.53 | 0.59 | 16.41 |
|  |  | LPA(L) | 8.11 | 3.16 | 8.37 | 5.27 | 0.10 | 20.98 |
|  |  | LPA(A) | 3.10 | 1.38 | 3.66 | 2.23 | 0.10 | 9.05 |
|  |  | LPA(D) | 0.10 | 0.00 | 0.00 | 0.10 | 0.10 | 0.10 |
| Cervical Carcinoma | 4 | LPA(P) | 8.64 | 3.25 | 6.50 | 9.20 | 0.86 | 15.29 |
|  |  | LPA(S) | 7.73 | 2.70 | 5.40 | 8.39 | 1.14 | 12.98 |
|  |  | LPA(O) | 4.52 | 1.84 | 3.69 | 4.86 | 0.10 | 8.27 |
|  |  | LPA(L) | 4.35 | 2.36 | 4.72 | 3.44 | 0.10 | 10.44 |
|  |  | LPA(A) | 4.43 | 2.02 | 4.05 | 4.32 | 0.10 | 8.97 |
|  |  | LPA(D) | 0.10 | 0.00 | 0.00 | 0.10 | 0.10 | 0.10 |
| Benign Gynecological Disease | 3 | LPA(P) | 0.10 | 0.00 | 0.00 | 0.10 | 0.10 | 0.10 |
|  |  | LPA(S) | 0.10 | 0.00 | 0.00 | 0.10 | 0.10 | 0.10 |
|  |  | LPA(O) | 0.10 | 0.00 | 0.00 | 0.10 | 0.10 | 0.10 |
|  |  | LPA(L) | 0.10 | 0.00 | 0.00 | 0.10 | 0.10 | 0.10 |
|  |  | LPA(A) | 0.10 | 0.00 | 0.00 | 0.10 | 0.10 | 0.10 |
|  |  | LPA(D) | 0.10 | 0.00 | 0.00 | 0.10 | 0.10 | 0.10 |
| Sarcoma | 4 | LPA(P) | 0.10 | 0.00 | 0.00 | 0.10 | 0.10 | 0.10 |
|  |  | LPA(S) | 0.60 | 0.50 | 0.99 | 0.10 | 0.10 | 2.08 |
|  |  | LPA(O) | 0.32 | 0.22 | 0.45 | 0.10 | 0.10 | 0.99 |
|  |  | LPA(L) | 0.43 | 0.33 | 0.67 | 0.10 | 0.10 | 1.43 |
|  |  | LPA(A) | 0.95 | 0.85 | 1.69 | 0.10 | 0.10 | 3.48 |
|  |  | LPA(D) | 0.10 | 0.00 | 0.00 | 0.10 | 0.10 | 0.10 |
| Breast Cancer | 11 | LPA(P) | 0.10 | 0.00 | 0.00 | 0.10 | 0.10 | 0.10 |
|  |  | LPA(S) | 0.10 | 0.00 | 0.00 | 0.10 | 0.10 | 0.10 |
|  |  | LPA(O) | 0.18 | 0.03 | 0.10 | 0.10 | 0.10 | 0.43 |
|  |  | LPA(L) | 0.10 | 0.00 | 0.00 | 0.10 | 0.10 | 0.10 |
|  |  | LPA(A) | 0.10 | 0.00 | 0.00 | 0.10 | 0.10 | 0.10 |
|  |  | LPA(D) | 0.10 | 0.00 | 0.00 | 0.10 | 0.10 | 0.10 |
| Leukemia | 4 | LPA(P) | 0.10 | 0.00 | 0.00 | 0.10 | 0.10 | 0.10 |
|  |  | LPA(S) | 0.10 | 0.00 | 0.00 | 0.10 | 0.10 | 0.10 |
|  |  | LPA(O) | 0.10 | 0.00 | 0.00 | 0.10 | 0.10 | 0.10 |
|  |  | LPA(L) | 0.10 | 0.00 | 0.00 | 0.10 | 0.10 | 0.10 |
|  |  | LPA(A) | 0.10 | 0.00 | 0.00 | 0.10 | 0.10 | 0.10 |
|  |  | LPA(D) | 0.10 | 0.00 | 0.00 | 0.10 | 0.10 | 0.10 |

LPA(P): palmitoyl - LPA
LPA(S): stearoyl - LPA
LPA(O): oleoyl - LPA
LPA(L): linolenyl - LPA
LPA(A): arachidyl - LPA
LPA(D): docosahexanyl - LPA
B.D.: below detection
N.A.: Not available

TABLE III

Average Concentration of Total LPA ($\mu$M) in the Plasma of Patients

| Diagnosis | N | Mean | SE | SD | Median | Min | Max |
|---|---|---|---|---|---|---|---|
| Healthy | 23 | 0.45 | 0.23 | 1.09 | 0.10 | 0.10 | 4.93 |
| Ovarian Carcinoma | 19 | 18.68 | 3.43 | 14.97 | 14.07 | 2.53 | 56.17 |
| Peritoneal Carcinoma | 9 | 16.93 | 6.79 | 20.37 | 12.08 | 0.10 | 63.21 |
| Endometrial Carcinoma | 7 | 33.17 | 7.51 | 19.86 | 29.82 | 3.95 | 63.23 |
| Cervial Carcinoma | 4 | 29.58 | 11.83 | 23.67 | 32.57 | 2.00 | 51.19 |
| Benign Gynecological Disease | 3 | 0.10 | 0.00 | 0.00 | 0.10 | 0.10 | 0.10 |
| Sarcoma | 4 | 4.83 | 1.05 | 5.04 | 3.62 | 0.10 | 19.92 |
| Breast Cancer | 11 | 0.13 | 0.03 | 0.10 | 0.10 | 0.10 | 0.43 |
| Leukemia | 4 | 0.10 | 0.00 | 0.00 | 0.10 | 0.10 | 0.10 |

LPA(P): palmitoyl - LPA
LPA(S): stearoyl - LPA
LPA(O): oleoyl - LPA
LPA(L): linolenyl - LPA
LPA(A): arachidyl - LPA
LPA(D): docosahexanyl - LPA
B.D.: below detection
N.A.: Not available As shown in Table I, detectable levels of total LPA were found in each of the patients with I, Stage II, Stage III or Stage IV ovarian carcinoma. Thus, every one of the patients diagnosed as having early stage ovarian carcinoma or late state ovarian carcinoma had detectable levels of LPA in her plasma. No false negatives were observed in any of the patients with ovarian carcinoma. The concentration of total LPA in subjects with Stage I and Stage II ovarian carcinoma ranged from 4.67 to 32.32 µM. The concentration of total LPA in subjects with Stage III and Stage IV carcinoma ranged from 2.53 to 56.17 µM. Moreover, detectable levels of stearoyl-LPA were found in all of the patients with ovarian carcinoma and detectable levels of the LPA species palmitoyl-LPA and oleoyl-LPA were found in 18 out of the 19 patients with ovarian carcinoma.

In contrast, 19 out of the 23 subjects who were characterized as being healthy, did not have detectable levels of LPA in their plasma. The remaining four healthy patients had low concentrations of LPA in their plasma, ranging from 0.42 to 4.93 µM. It is not known whether these values represent false positives or whether these individuals had a gynecological carcinoma that was not detected by the other routine procedures used to diagnose the patients. Moreover, the average concentration of total LPA and of each LPA species in the plasma of patients diagnosed as having ovarian carcinoma was significantly higher than the average concentration of total LPA and of each LPA-species in the plasma of healthy patients. These results establish that the present method is highly sensitive and therefore useful for identifying those patients with the gynecological carcinoma of ovarian carcinoma, including those patients whose ovarian carcinomas are still in the early stages of development. The results also indicate that a method which detects the presence of palmitoyl LPA or stearoyl-LPA or oleoyl-LPA or combinations thereof in the plasma of patients is also useful for detecting ovarian carcinomas.

LPA was also detected in the plasma of every one of the subjects diagnosed as having cervical carcinoma and endometrial carcinoma, and in eight out of the nine subjects diagnosed as having peritoneal carcinoma. The peritoneal carcinoma had been totally debulked in the one patient who did not have detectable levels of LPA in her plasma. This result suggests that LPA is not present in the plasma of patients whose carcinomas are completely removed by surgery. Thus, the present method is useful for monitoring the recurrence of gynecological carcinomas in patients who have undergone surgical removal of the carcinoma. The concentration of LPA in the plasma of the subjects with cervical carcinoma and endometrial carcinoma ranged from 2.00 to 63.23 µM.

In contrast, detectable levels of LPA were not present in 15 out of the 17 patients diagnosed as having a cancer other than a gynecological carcinoma, i.e., breast cancer, leukemia, and uterine sarcoma. Moreover, detectable levels of LPA were not present in any of the subjects with uterine fibroids, a benign gynecological disease. Since plasma from three out of the four patients with gynecological sarcomas, which are derived from connective tissues, and with benign uterine fibroids did not have detectable levels of total LPA in their plasma, it is believed that malignant epithelial cells of the respective gynecological organ may be the source of the LPA in the plasma of patients with ovarian carcinoma, cervical carcinoma, endometrial carcinoma, and peritoneal carcinoma.

Because of its sensitivity, simplicity, and low cost, the present method is useful for screening patients for gynecological carcinomas. Because the blood specimens for the present method and for CA 125 testing can be drawn from a patient at the same time, CA 125 testing can also be performed when patients are screened for gynecological carcinomas by the present methods. Alternatively, the present method can be used alone to detect gynecological carcinomas.

Because the LPA is not present in the plasma of patients with benign gynecological diseases, the present method is also useful for distinguishing between gynecological diseases which are benign and gynecological diseases which are malignant in patients with gynecological masses. Use of this method to discriminate between malignant and benign ovarian masses should reduce the number of patients required to undergo the more expensive techniques such as transvaginal sonography or the more invasive techniques such as tumor biopsy or tumor aspiration that are now used to diagnose ovarian tumor malignancy.

EXAMPLE 2

Sample Collection from Patients and Healthy Controls

Samples were collected from 9 patients who were seen in the Department of Gynecology and Obstetrics at the Cleveland Clinic Foundation between February 1998 and April 1998. Whole blood specimens were obtained from 8 patients (median age, 65.0 years; range 44–72 years) with ovarian cancer, 1 patients with endometrial cancer (age 44 years), and 10 healthy controls (median age, 45.5 years, range 28–48 years). An informed consent was obtained form all participants.

All of the cancer patients had been diagnosed with cancer when blood samples were drawn. Clinical stage was determined according to the International Federation of Gynecologists and Obstetricians (FIGO) criteria, and the histological subtype was evaluated according to the WHO classification. (See Table IV below.) To prevent platelet activation and phospholipase activity, blood samples were collected in EDTA-containing tubes. Whole blood was centrifuged at 2,500 g for 15 minutes. Plasma was either processed immediately or stored at −80° C. before lipid extraction.

TABLE IV

The clinical data

| Subject # | Age | Healthy Conditions | Stage | Grade | Subtype | CA125 |
|---|---|---|---|---|---|---|
| 1 | 41 | Healthy | | | | |
| 2 | 37 | Healthy | | | | |
| 3 | 45 | Healthy | | | | |
| 4 | 46 | Healthy | | | | |
| 5 | 32 | Healthy | | | | |
| 6 | 48 | Healthy | | | | |
| 7 | 28 | Healthy | | | | |
| 8 | 47 | Healthy | | | | |
| 9 | 45 | Uterine fibroids | | | | |
| 10 | 44 | Uterine fibroids | | | | |
| 11 | 55 | | IIC | 2 | Endometrioid | 37 |
| 12 | 67 | | IV | 3 | Serous | 201 |
| 13 | 64 | | III | 3 | Endometrioid | 1284 |
| 14 | 46 | | III | 3 | Serous | 46 |
| 15 | 66 | | IIIC | 3 | Serous | 1091 |
| 16 | 66 | | IV | 3 | Serous | 909 |
| 17 | 72 | | III | 3 | Serous | 11 |
| 18 | 61 | | III | 3 | Serous | 447 |
| 19 | 44 | | III | | | |

Subjects # 11 to 18 were patients with ovarian cancer and subject # 19 was a patient with endometrial cancer.

Reagents and Standards

LPA and other lysophospholipids, except 16:0-LPI, were purchased from Avanti Polar Lipids (Birmingham, Ala.) The LPI preparation (extracted from soybean and contains 62% 16:0-LPI; cat. #L-7635, lot #46H8390;) was from Sigma (St. Louis, Mo.). Precoated silica gel 60 TLC plates were obtained from EM Science (Gibbstown, N.J.). HPLC grade methanol (MeOH), chloroform, ammonium hydroxide (AmOH), hydrochloric acid (HCl) were purchased from Sigma (St. Louis, Mo.) or Fisher Scientific Co. (Pittsburgh, Pa.)

LPA-17:0 was purchased from Avanti in chloroform form. Known amounts of the lipid were aliquoted in a known amount and the chloroform was evaporated under $N_2$ at 40° C. The lipid was resuspended in methanol and 500 pmol was added to each sample before the lipid extraction. LPAs-16:0, 18:0 and 18:1 and LPI (18:0) were obtained from Avanti and standard solutions were made in methanol. To obtain standard curves, different amounts (5–300 pmol) of standard LPAs or 18:0-LPI were mixed with the same amount (50 pmol) of internal standard LPA-17:0.

Preparation of Samples

Blood samples were centrifuged at 2,500 g for 15 min at 4° C. The plasma was transferred into siliconized eppendorf tubes and frozen at −80° C. or used immediately. All extraction procedures were performed in 15 ml glass disposable centrifuge tubes (Supelco/Sigma,. St. Louis, Mo.). For each 1 ml of blood sample, 0.2 ml of 6N HCl and 4 ml MeOH/Chloroform (2:1) were added. The sample was vortexed for 1 min and incubated on ice for 10 min. One ml chloroform and 1.25 ml $H_2O$ were added to separate the phases. The samples were vortexed for 0.5 min and incubated on ice for 0.5 min. After centrifugation (2000 g for 10 min), the lower phase was transferred to a new glass tube and the solvent was evaporated under nitrogen at 40° C. in a React-Therm (Pierce, Rockford, Ill.). The dried lipids were resuspended in 501 µL solvent (MeOH: chloroform 2:1), vortexed and applied to a TLC plate.

The silica gel 60 TLC plates were pre-run using the solvent system (chloroform:MeOH:AMOH=65:35:5.5) to remove contaminants and then dried. Samples were applied to TLC plates as a band and developed in the same solvent system. One each TLC plate, two markers: standard oleoyl-LPA (18:1) were always applied to help in identifying the "LPA band". The lipids in the "LPA band" were eluted with 2 ml MeOH: chloroform (2:1) twice, dried under nitrogen at 40° C. and resuspended in 100 µL of 100% MeOH. This sample was directly used in ESI-MS (20 µL for each injection).

Validations

ESI-MS and ESI-tandem MS (MS-MS) were performed to confirm the structures and identities of the ion peaks of interest. The method of quantitation were developed using commercially available standards. The internal standard, 17:0-LPA, was chosen due to the absence of ion species in the m/z range of 423 in blood samples, and because 17:0-LPA is not a naturally occurring LPA species.

ESI-MS Conditions

The ESI-MS and tandem mass spectrometry (MS/MS) were performed on a Micromass Quattro II Triple Quadrupole Mass Spectrometer equipped with an ESI source (Micromass Inc. Beverley, Mass.). The samples were delivered into the ESI source using a LC system (HP 1100) with an injection valve (20 µL injection loop) via a 125 µm PEEK tubing. The mobile phase used for all experiments was MeOH:$H_2O$ (1:1;v:v) and the flow rate was 50 µL/min.

The instrument settings used are as follows: the ionspray interface was maintained at 70° C. with a nitrogen nebulization flow of 10 L/h. The ESI drying gas ($N_2$) was at 250 L/h. For the product (79) or (184) scan modes with negative or positive detection, the argon (as collision gas) was at a pressure of $10 \times 10^6$ bar or $1 \times 10^{-5}$ bar; the ionspray voltages were −3,500 V or 3,500 V; the counter electrode potentials were −500V or 500V; the sample cone potentials were −50V or 20V; the collision energies were 70 or 50 eV; and the skimmer voltages were −1.0 or 2.0V, respectively. The product (79) scan mode with negative ion detection was used in all standard and sample analyses. Detection of LPA and other related lyso-PLs in the "LPA band" of plasma samples.

Ion species were detected in the range of m/z 400–7000. This range includes all major species of lysophospholipids, but exclude di- or tri-plysphate-1PIs (>700, which were absent in the "LPA band."

Figure 1:
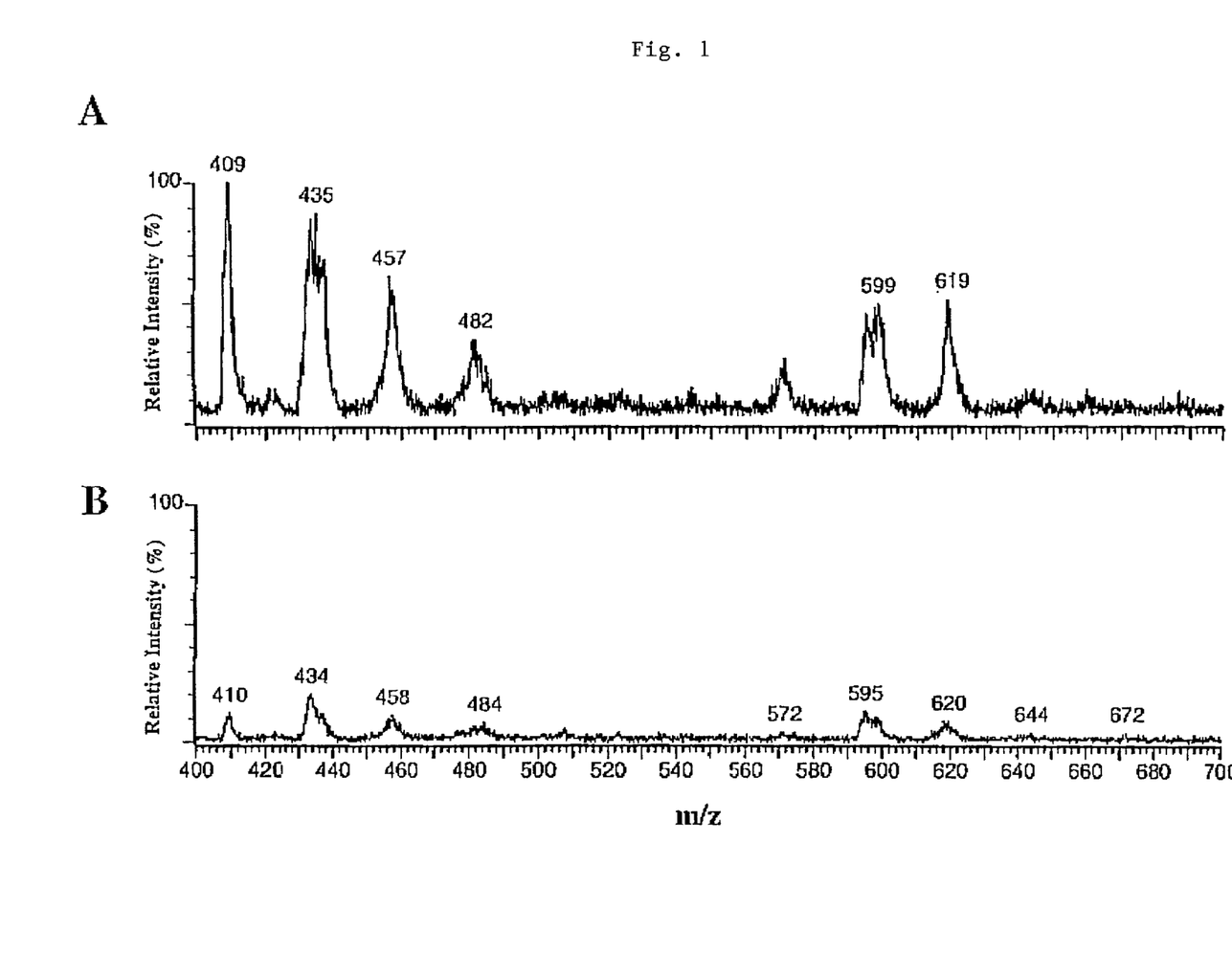

FIG. 1 show the representative mass spectra of lysophospholipids from patient with ovarian or peritoneal cancer (FIG. 1A) or healthy controls (FIG. 1B) The major ions and their identities are 409 (16:0-LPA), 433–437 (18:2, 18:1 and 18:0-LPAs, 457, 481–482, 571 (16:0-LPI), 599 (18:0-LPI) and 619 (20:4-LPI). Patients with either ovarian or peritoneal cancer had higher levels of both LPA and LPI as compared to healthy controls.

The identities of these ion species were achieved through three steps: 1) the m/z of the ion species; ii) the presence of the phosphoroyl group [detected in the product (79) scan mode]; and iii) MS-MS analysis of the daughter ions of these species in negative detection mode. For 16:0-LPA, the major products were the phosphoryl group $PO_3^-$ ion (at m/z 790), $PO_4H_2^-$ ion (at m/z 97), glycerol phosphoryl $C_3H_6O_2PO_3^-$ ion (at m/z 153), O-glycerol phosphoryl $C_3H_6O_3PO_4H_2^-$ ion (at m/z 171), palmitic acid ($C_{16}H_{31}O_2^-$, at m/z 255) (FIG. 5A). LPI (18:0) mainly showed the $PO_3^-$, $PO_4H_2^-$, glycerol phosphate $C_3H_6O_2PO_3^-$, phosphoinositol $C_6H_{10}O_6PO_2^-$ ion (at m/z 241), and stearic acid ($C_{18}H_{35}O_2^-$ at m/z 283) ions. LPS mainly showed the $PO_3^-$, $PH_4H_2^-$, glycerol phosphate $C_3H_6O_2PO_3^-$, O-glycerol phosphoryl $C_3H_6O_2PO_4H_2^-$, oleic acid ($C_{18}H_{33}O_2^-$ at m/z 281) and 18:1-LPA (loss of serine; at m/z 435). Ion species at 435, 437, 571 and 619 also showed expected daughter ions.

Optimal ionization conditions for simultaneously detecting LPAs and LPIs in blood samples were tested. While 0.5 mM $NH_4OH$ did not affect the ionization efficiency of LPAs, it slightly reduced the ionization efficiency of LPI. Addition of 5 mM ammonium acetate reduced the ionization efficiency of LPAs to approximately 40%, but increased the ionization efficiency of LPI to approximately 30%. To balance the simultaneously detection efficiency for both LPAs and, LPIs, we chose to use MeOH without any additives.

We examined the levels of LPAs and LPIs in a series of plasma sample dilutions (0.1, 0.2, 0.4, 0.5, 0.6, 0.8 and 1 ml) and found that the detected levels of LPAs and LPIs were linear in this range, therefore 0.5 ml of plasma samples were used in our later studies.

Quantitative Analysis of LPAs and LPIs in Blood Samples

To perform quantitative analysis of levels of LPA and LPI, we established standard curves using the ratios of different amount (5–300 pmol) of a combination of standard 14:0-LPA, 16:0-LPA, 18:0-LPA, 18:1-LPA, 16:0-LPI (Sigma) and 18:0-LPI to a fixed amount (50 pmol) of the internal standard 17:0-LPA (Avanti). The areas of each ion species were obtained from the chromatogram. To determine whether different LPI species have different ionization efficiencies, we used the natural LPI isolated from soybean, which contains 62% 16:0-LPI as analyzed by Sigma using a GC-based analysis (cat. #L-7635, lot #46H8390). All LPAs and LPIs displayed linear curves in the concentration range tested. The slopes of standard curves for different LPA species were different. Surprisingly, we found that the LPA with longer fatty acid side chains had higher ionization efficiencies, compared with shorter ones. This is reflected by their higher slopes. The slopes of 18:0-LPA and 18:1-LPA were very similar, suggesting that the double bond did not affect ionization efficiency significantly. Plotting the slopes for 14:0-LPA, 16:0-LPA and 18:0-LPA against the length of their side chains, a linear relationship was obtained. By extending this curve, we obtained the theoretical slopes for 20:4-LPA (2.12) and 22:6-LPA (2.50). These values were used in calculations for the total LPA levels. In addition, the slope (1.73) for 18:1-LPA was used for 18:2-LPA calculations. A similar trend was observed in the LPI series. Therefore a theoretical slope (1.21) was deduces for 20:4-LPI and used for the calculations.

Figure 2:
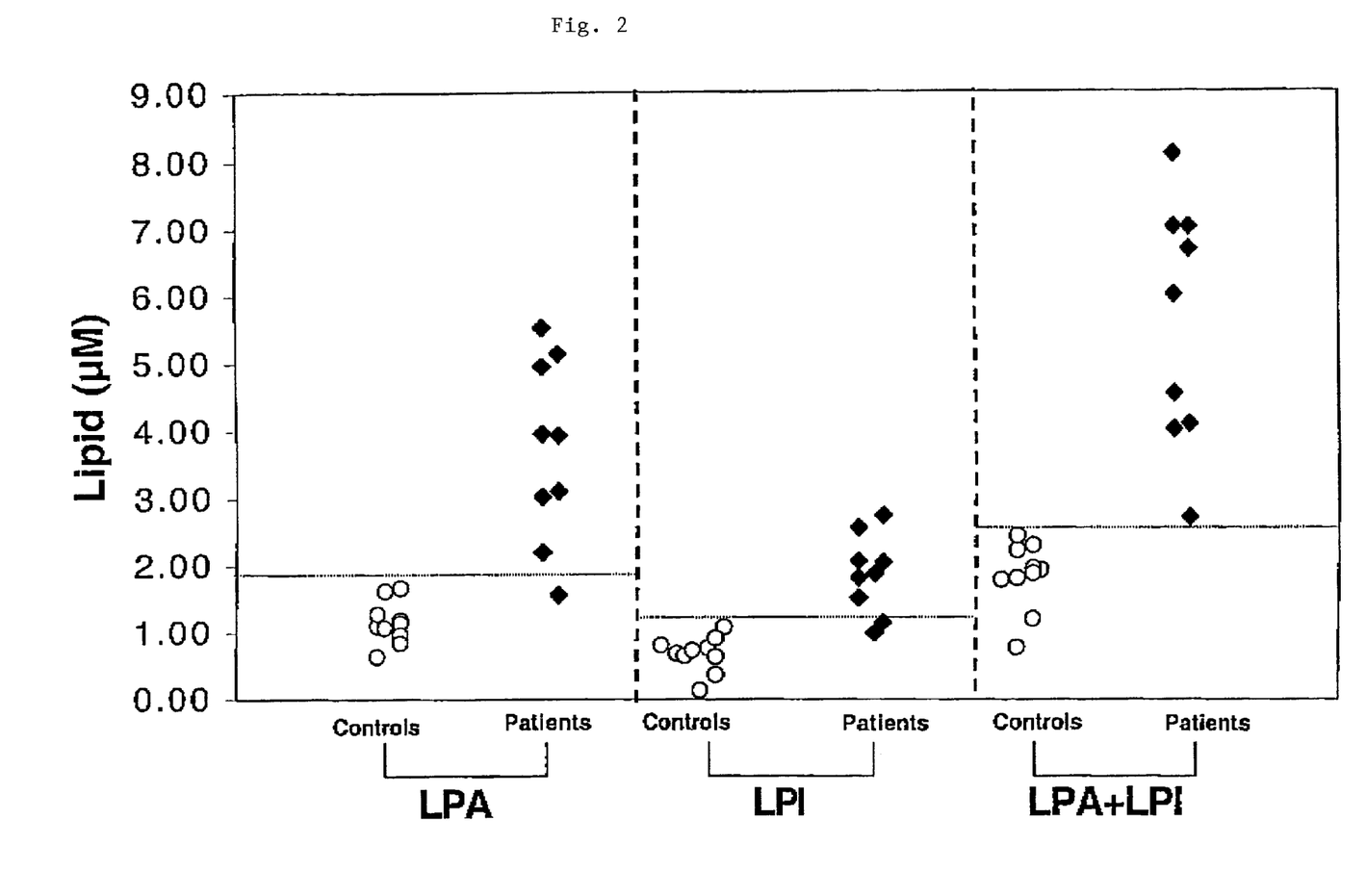
FIG. 2 is a scatter plot showing total plasma LPA, LPI and LPA+LPI levels from healthy control subjects and from patients with ovarian and endometrial carcinoma.

We applied the established method to the analysis of plasma samples from 9 patients with either ovarian (8) or endometrial cancer (1) and 8 healthy female controls and two women with benign gynecological disease (uterus fibroids). Total plasma LPA, LPI and LPA+LPI levels from these subjects are shown in FIG.2 The patients group clearly showed higher levels of both LPA and LPI levels, and levels of total LPA and LPI apparently separated better between patients and control groups than either LPA or LPI alone.

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto.

What is claimed:

1. A method of diagnosing ovarian carcinoma in a subject comprising: assaying for the presence of lysophosphatidyl inositol in a bodily fluid from the subject; determining the level of lysophosphatidyl inositol in said bodily fluid to provide a test value; and comparing the test value to a standard value, wherein a test value above the standard value is indicative of ovarian carcinoma.

2. The method of claim 1 wherein said bodily fluid is blood.

3. The method of claim 1 further comprising the step of determining the level of lysphosphatidic acid in said fluid to provide a combined test value, wherein the combined test value is based on the level of lysphosphatidic acid and the level of lysophosphatidyl inositol in said bodily fluid; and comparing the combined test value to a combined standard value, wherein a combined test value above the combined standard value is indicative of ovarian carcinoma.

4. A method of diagnosing ovarian carcinoma in a subject comprising: assaying for the presence of lysophosphatidyl inositol in a plasma sample from the subject; determining the level of lysophosphatidyl inositol in said plasma sample to provide a test value; and comparing the test value to a standard value, wherein a test value above the standard value is indicative of ovarian carcinoma.

5. The method of claim 4 further comprising the step of determining the level of lysophophatidic acid in said plasma sample to provide a combined test value, wherein the combined test value is based on the level of lysophosphatidic acid and the level of lysophposphatidyl inosoitol is said plasma sample; and comparing the combined test value to a combined standard value, wherein a combined test value above the combined standard value is indicative of ovarian carcinoma.

* * * * *